US012642649B2

(12) United States Patent
Dibie

(10) Patent No.: US 12,642,649 B2
(45) Date of Patent: Jun. 2, 2026

(54) ASSEMBLY FOR REPLACING THE TRICUSPID ATRIOVENTRICULAR VALVE

(71) Applicant: T-Heart SAS, Paris (FR)

(72) Inventor: Alain Dibie, Paris (FR)

(73) Assignee: T-HEART SAS, Paris (FR)

( * ) Notice: Subject to any disclaimer, the term of this patent is extended or adjusted under 35 U.S.C. 154(b) by 0 days.

(21) Appl. No.: 17/491,642

(22) Filed: Oct. 1, 2021

(65) Prior Publication Data

US 2022/0015901 A1 Jan. 20, 2022

Related U.S. Application Data

(63) Continuation of application No. 15/777,177, filed as application No. PCT/EP2016/077715 on Nov. 15, 2016, now Pat. No. 11,154,396.

(30) Foreign Application Priority Data

Nov. 23, 2015 (FR) ...................................... 1561217

(51) Int. Cl.
    *A61F 2/24* (2006.01)
(52) U.S. Cl.
    CPC .......... *A61F 2/2418* (2013.01); *A61F 2/2427* (2013.01); *A61F 2210/0014* (2013.01);
    (Continued)
(58) Field of Classification Search
    CPC .................. A61F 2/2418; A61F 2/2427; A61F 2210/0014; A61F 2220/0008;
    (Continued)

(56) References Cited

U.S. PATENT DOCUMENTS 8,512,396 B2   8/2013 Styrc
8,657,872 B2   2/2014 Seguin
(Continued)

FOREIGN PATENT DOCUMENTS

CN   103974674 A   8/2014
EP   2861166 A1   4/2015
(Continued)

OTHER PUBLICATIONS

European Search Report issued in European application No. 16795096.3, dated Sep. 18, 2020.
(Continued)

*Primary Examiner* — Alexander J Orkin
(74) *Attorney, Agent, or Firm* — Nicola A. Pisano; Cozen O'Connor

(57) ABSTRACT

An assembly for the tricuspid orifice of a human heart has an external frame connected to an internal stent carrying a tricuspid valve bioprosthesis and a sealing skirt. The external frame is configured to hold its position in the native tricuspid annulus. The internal stent is connected to the external frame by one or more fixing strands. The sealing skirt covers the interstitial space existing between the external frame and the internal stent. Developments are described which include the use of a deformable region of the frame, various alternative embodiments of the sealing skirt, the use of a frame composed of multiple sub-sections, the use of fixing strands between the stent and the frame and of fixing elements for fixing the assembly to the native tissue, the use of sensors and/or actuators, and also the use of a stent in the inferior vena cava. Method aspects are also described.

24 Claims, 9 Drawing Sheets

(52) U.S. Cl.
CPC ................. *A61F 2220/0008* (2013.01); *A61F 2220/0075* (2013.01); *A61F 2230/0008* (2013.01); *A61F 2230/0013* (2013.01); *A61F 2250/0098* (2013.01)

(58) Field of Classification Search
CPC ...... A61F 2220/0075; A61F 2230/0008; A61F 2230/0013; A61F 2250/0098
See application file for complete search history.

(56) References Cited

U.S. PATENT DOCUMENTS

| | | | |
|---|---|---|---|
| 8,845,722 | B2 | 9/2014 | Gabbay |
| 10,299,921 | B2 | 5/2019 | Dale et al. |
| 11,154,396 | B2 * | 10/2021 | Dibie .................... A61F 2/2418 |
| 2003/0014104 | A1 * | 1/2003 | Cribier ................. A61F 2/2412 623/2.14 |
| 2006/0052867 | A1 * | 3/2006 | Revuelta .............. A61F 2/2409 623/2.38 |
| 2006/0195183 | A1 * | 8/2006 | Navia ................... A61F 2/2418 623/2.11 |
| 2009/0171456 | A1 | 7/2009 | Kveen et al. |
| 2009/0287299 | A1 * | 11/2009 | Tabor ................... A61F 2/2418 623/1.26 |
| 2010/0100176 | A1 * | 4/2010 | Elizondo .............. A61F 2/2418 623/2.38 |
| 2010/0217382 | A1 | 8/2010 | Chau et al. |
| 2010/0312333 | A1 | 12/2010 | Navia et al. |
| 2011/0022157 | A1 * | 1/2011 | Essinger .............. A61F 2/2418 623/1.11 |
| 2011/0029072 | A1 * | 2/2011 | Gabbay ................ A61F 2/2418 623/2.37 |
| 2011/0054519 | A1 * | 3/2011 | Neuss ............. A61B 17/12177 606/213 |
| 2012/0022633 | A1 | 1/2012 | Olson |
| 2013/0204357 | A1 | 8/2013 | Thill et al. |
| 2013/0304200 | A1 * | 11/2013 | McLean ............... A61F 2/2418 623/2.18 |
| 2014/0172070 | A1 | 6/2014 | Seguin |
| 2014/0194983 | A1 | 7/2014 | Kovalsky et al. |
| 2014/0222142 | A1 | 8/2014 | Kovalsky et al. |
| 2014/0249622 | A1 * | 9/2014 | Carmi ................... A61F 2/2418 623/2.11 |
| 2014/0277427 | A1 * | 9/2014 | Ratz ...................... A61F 2/2409 623/2.38 |
| 2015/0112430 | A1 | 4/2015 | Creaven et al. |
| 2015/0142100 | A1 * | 5/2015 | Morriss .................. A61F 2/246 623/2.4 |
| 2015/0173897 | A1 * | 6/2015 | Raanani ............... A61F 2/2418 623/2.11 |
| 2015/0327996 | A1 * | 11/2015 | Fahim ..................... A61F 2/844 623/2.17 |
| 2015/0328000 | A1 * | 11/2015 | Ratz ...................... A61F 2/2418 623/2.37 |
| 2015/0359629 | A1 | 12/2015 | Ganesan et al. |
| 2016/0310267 | A1 * | 10/2016 | Zeng ..................... A61F 2/2409 |
| 2016/0354201 | A1 * | 12/2016 | Keogh .................. A61F 2/2418 |
| 2018/0333259 | A1 | 11/2018 | Dibie |

FOREIGN PATENT DOCUMENTS

| | | |
|---|---|---|
| JP | 2008-536592 A | 9/2008 |
| JP | 2008539985 A | 11/2008 |
| JP | 2013543406 A | 12/2013 |
| JP | 2015-517854 A | 6/2015 |
| JP | 2017538540 A | 12/2017 |
| JP | 2018535074 A | 11/2018 |
| JP | 2019506937 A | 3/2019 |
| WO | 2006/111391 A1 | 10/2006 |
| WO | 2009/044082 A2 | 4/2009 |
| WO | 2012/178115 A2 | 12/2012 |
| WO | 2013/177684 A1 | 12/2013 |
| WO | 2014144937 A2 | 9/2014 |
| WO | 2015/107226 A1 | 7/2015 |
| WO | 2015/188066 A1 | 12/2015 |
| WO | 2016098104 A2 | 6/2016 |
| WO | 2016/130913 A1 | 8/2016 |
| WO | 2017089179 A1 | 6/2017 |

OTHER PUBLICATIONS

Japanese Office Action issued in Japanese application No. 2018-545550, dated Dec. 1, 2020.

* cited by examiner

ASSEMBLY FOR REPLACING THE TRICUSPID ATRIOVENTRICULAR VALVE

REFERENCE TO RELATED APPLICATIONS

This application is a continuation of U.S. patent application Ser. No. 15/777,177, filed May 17, 2018, which is a National Stage of International patent application PCT/EP2016/077715, filed Nov. 15, 2016, which claims priority to France patent application No. FR 1561217, filed Nov. 23, 2015. The entire content of each application is incorporated herein by reference.

FIELD OF THE INVENTION

The invention relates to the field concerned with methods and systems for replacing a defective atrioventricular heart valve or tricuspid valve.

BACKGROUND OF THE INVENTION

The human heart has four heart valves. Two of these valves are called the atrioventricular valves. The tricuspid valve is situated between the right atrium and the right ventricle. The mitral valve is situated between the left atrium and the left ventricle. The other two valves are situated between the ventricles and the vascular system. The aortic valve separates the left ventricle from the aorta, and the pulmonary valve separates the right ventricle from the pulmonary artery.

In some medical situations, it may be appropriate to repair or replace the tricuspid valve. These medical indications are mainly due to a functional pathology of the tricuspid valve, which pathology may be elusive, severe, and secondary to a significant dilation of the tricuspid annulus. More rarely, this pathology is due to a rheumatic or infectious valvular disease or even to degeneration of a stenosing or leaking bioprosthesis.

Many systems have been described to permit replacement of defective heart valves, in particular by a percutaneous route or by a minimally invasive route.

Techniques are known in particular for replacement of the mitral valve. By contrast, very few scientific documents and a fortiori patent documents deal with the orthotopic replacement of the tricuspid valve.

The technical teachings published with regard to replacement of the mitral valve are not directly transferable to the case of replacement of the tricuspid valve, in particular for physiopathological reasons (the anatomy of the tricuspid annulus is only slightly fibrous by nature, its dimensions are greater and ovoid; the anatomy of the right ventricle is also particular).

The tricuspid valve is substantially larger than the mitral valve. In pathological situations, the tricuspid annulus dilates to a diameter in excess of 40 mm, while the pathological mitral annulus measures about 30 to 35 mm. This difference has several consequences, especially mechanical ones (e.g. support, stability, and regarding peri-prosthetic leaks).

However, the converse is generally conceivable: the techniques applicable to the tricuspid valve could be applicable a fortiori to the mitral valve.

The patent literature reports documents claiming to apply equally to both types of atrioventricular valves, but in reality these technical teachings can generally be applied only in the case of the mitral valve.

The patent documents US2014/0172070 and U.S. Pat. No. 8,657,872 are examples of such documents, for which the described technical teachings have limitations and/or shortcomings and/or inadequacies as regards applications to the replacement of the tricuspid valve.

Although close anatomically, the aortic valve and the pulmonary valve in fact have characteristics requiring different treatment and/or replacement methods, if only in view of their anatomical situation in the heart.

In clinical practice, only the aortic valve is at present routinely replaced by a percutaneous valve. Bioprosthesis models for the percutaneous mitral valve are currently in the process of clinical evaluation. Regarding the tricuspid valve, while valvuloplasty and annuloplasty (narrowing of the native annulus) operations are known, clinical treatments involving a percutaneous orthotopic bioprosthesis are in the course of development and at a very early stage.

The invention falls within this latter development.

There is a need for methods and systems specifically adapted to the replacement of the tricuspid valve.

SUMMARY OF THE INVENTION

The present invention discloses systems for replacing the atrioventricular tricuspid valve. According to the invention, a frame comprises a stent, which itself contains the tricuspid valve bioprosthesis. The diameter of the frame is therefore greater than that of the stent, which carries the bioprosthesis. In a particular embodiment, the diameter of the frame is slightly greater than that of the stent, which is itself adapted to the diameter of the bioprosthesis.

The present invention also discloses methods for replacing the atrioventricular tricuspid valve. The route is generally a percutaneous trans-catheter route. After a percutaneous approach, the system contained in a catheter is put into place by a vascular route.

An assembly for the tricuspid orifice of a human heart is disclosed, comprising an external frame connected to an internal stent which carries a tricuspid valve bioprosthesis and a sealing skirt, and in which assembly the external frame is adapted to hold its position in the native tricuspid annulus (potentially and/or when deployed in a patient's heart); the internal stent is connected to the external frame by one or more fixing strands; and the sealing skirt covers the interstitial space existing between the external frame and the internal stent (in the packaged state and/or when deployed in the heart of a patient).

In one development, the sealing skirt further covers the (contact) space existing between the external frame and the site of the native tissue (i.e. potentially, i.e. in a folded or packaged state) and/or the native tissue (i.e. in a situation deployed in a patient's heart) in the region of the annulus.

In one embodiment, the sealing skirt effects a fold or a return, making it possible both to obstruct the space of contact with the native tissue and to cover the interstitial space between the frame and the stent upstream from the annulus.

In one embodiment, the skirt covers only this interstitial space, and other means are used to prevent peri-prosthetic leaks (e.g. a sealing band or bead, biocompatible adhesive or filler material, etc.).

The frame is prestressed or, by virtue of its structure, exerts a radial force (directed radially outward), which allows it to be held in position in the native annulus. The frame carries or comprises or is associated with a stent, which itself carries or comprises or is associated with a bioprosthesis. The sealing skirt makes it possible to channel the blood flow from the right atrium to the right ventricle through the bioprosthesis (by covering the "interstitial" space (which is still non-zero) existing between the frame and the stent carrying the bioprosthesis with a diameter selected from a limited choice). The sealing skirt also makes it possible to minimize (or even entirely avoid) peri-prosthetic leaks between the frame and the native tissue (by covering and/or blocking and/or obstructing, in the region of the annulus, the "contact" space existing between the external frame, pressed against the native tissue, and the native tissue. The blood flow is obstructed (or stopped or blocked or obstructed or prevented) over the entire circumference on the width of the "contact" space by the leaktight skirt.

In one development, the frame has a deformable region in the region corresponding to the native annulus.

In one development, the frame covered by the sealing skirt moreover has, upstream from the region of the native annulus, a shape that reinforces the hold of the assembly in the native annulus.

The shape can be convex or flared so as to optimize the capture of the blood flow, which contributes to stabilizing or maintaining the hold of the assembly in the tricuspid annulus (appropriate capture minimizes the mechanical effects of torsion, i.e. of rotation/translation of the assembly that the blood pressure could cause due to the presence of the leaktight skirt).

In one development, the frame further has, downstream from the region of the native annulus, a shape that minimizes the disruption of the flow of the blood.

Generally, the part of the frame that penetrates the region of the right ventricle is limited in its dimensions (cf. the orders of magnitude given below). In some embodiments, the function of the shape of this part of the frame can minimize the turbulence (e.g. special shapes can in particular involve drag effects which tend to give a more laminar flow of the blood).

In one development, the frame comprises a plurality of sub-sections.

In one embodiment, the frame is in one piece, that is to say formed integrally (for example, the frame is printed in 3D from a deformable material). In one embodiment, the frame is composed of two sub-sections (for example complementary or symmetrical). In one embodiment, the frame is composed of three parts (in an economical and robust arrangement). In one embodiment, the frame is composed of four sub-sections (symmetrical arrangement, advantageous in terms of stability). In a particular embodiment, the frame is composed of a large number of sub-sections or frame wires.

In one embodiment, the different sub-sections of the frame are integral with each other. In one embodiment, the different sub-sections of the frame are at least partially independent of one another. In some embodiments, at least one sub-section of the frame has a physical property chosen from among the properties including rigidity, elasticity, plasticity, shape memory, heat-sensitive, actuatable, instrumented, configurable and sprung.

In one development, the external frame is connected to the internal stent by one or more strands.

In one development, the frame comprises four sub-sections, each of the sub-sections being connected to the internal stent by a strand made of nitinol.

The configuration with four sub-sections and four strands makes the assembly particularly stable against the effects of mechanical torsion. Other embodiments comprise one or more "crossed" links between the sections of the frame with one another and/or with the stent.

In one development, the assembly further comprises at least one fixing element for fixing to the native tissue.

The element for fixing to the native tissue improves in particular the hold of the assembly in translation and/or rotation, being nearest to the region of the native annulus.

In one development, the arrangement of the sealing skirt is configurable or reconfigurable or repositionable, for example by means of an actuator.

For example, the spatial arrangement of the skirt can be adapted to the variations in the space existing between the stent of the bioprosthesis and the frame. The skirt can to some extent be actuated or repositioned, for example remotely.

In one development, the frame and/or the stent and/or a fixing strand and/or a fixing element are made of a heat-sensitive and/or shape-memory material.

In one development, the assembly further comprises at least one sensor and/or a marker.

The sensor can in particular be a position sensor, a movement sensor, a pressure sensor or a chemical and/or biological sensor (biomarker). The marker can in particular be a radiopaque marker.

In one development, the assembly further comprises an actuator suitable for modifying the structure of the assembly and/or for adjusting the positioning of part of the assembly with respect to the native annulus.

The assembly can be articulated or articulatable. The repositioning can be relative (with respect to the native tissue) and/or absolute (modification to the shape of the structure of the assembly itself). This reconfiguration can be manual and/or automatic.

In one development, the assembly is connected to a stent suitable for placement in the inferior vena cava, this stent being connected to the frame of the assembly by a strand made of nitinol.

In one development, the assembly is folded in a packaged state in a catheter for introduction by a percutaneous route (e.g. by a vascular route or by a trans-cardiac route).

A method for replacing the tricuspid valve is disclosed, comprising steps which involve positioning the assembly in a folded state in a catheter, and introducing and deploying said assembly by a percutaneous route.

Advantageously, the interstitial space or gap (between the frame of variable diameter and the stent of standardized size, that is to say of discrete sizes and situated inside the frame) is of variable dimension.

Advantageously, the stent is fixed to the frame (for example on the atrial side) by one or more strands, for example made of nitinol.

Advantageously, the shape of the frame comprises three zones, one of which zones is situated in the region of the native annulus; the frame bears against the native cardiac tissue of the tricuspid annulus and holds the assembly in position by its radial force.

Advantageously, according to some embodiments, the stent containing or carrying the bioprosthesis is positioned asymmetrically with respect to the annulus (predominantly in the atrium and barely present in the right ventricle).

Advantageously, the intrusions in the right ventricle are minimized, in particular so as not to disturb the flow of the blood circulation.

Advantageously, some optional embodiments of the invention comprise a system for holding in translation (presence of a stent in the anastomosis of the inferior vena cava, presence of one or more fixing elements for fixing to the native tissue), in particular not disrupting the flow of blood.

Advantageously, various embodiments of the invention permit the placement of a sealing skirt. The presence of this sealing skirt makes it possible in particular to minimize or prevent peri-prosthetic leaks between the assembly and the native tissue. The sealing skirt can be made of PET (polyethylene terephthalate) or of another material impervious to blood, covering the height of the annulus and covering the base of the frame on the atrial side.

Advantageously, the embodiments of the invention make it possible to streamline clinical practice, with many proven or potential spin-off effects (economies of scale, standardization of the operations, increased safety, etc.). The valve bioprostheses currently on the market are usually "standardized", i.e. the various existing valve ranges are limited, and the valves are of discrete dimensions (generally 35 mm, 40 mm and 45 mm). Customization (of the bioprosthesis) is possible, but it is expensive and presents certain risks inherent to the manufacture of a non-standard prosthesis. The embodiments of the invention make it possible to avoid having to adjust the dimensions of the valve itself to the exact dimensions of the tricuspid annulus.

The dimensions of the frame, on the one hand, and of the stent/bioprosthesis, on the other hand, define the dimensions of the interstitial space (gap) existing between the frame and the stent/bioprosthesis device. This space can be of a greater or lesser extent, generally of a few millimeters, depending on the configurations and/or the requirements. For example, the diameter of the stent can be of the order of 20% less than the diameter of the frame at the native annulus (in this configuration, the sealing skirt plays a central role in channeling the blood flow and in eliminating leaks between the stent and the frame). In another case, the diameter of the stent can be closer to the diameter of the frame at the native annulus, with the sealing skirt covering the space between the frame and the stent.

Several adjustment variables exist according to the embodiments of the invention, in particular the diameters of the frame and the diameter of the stent carrying the bioprosthesis, which diameters are measured at the native annulus. One adjustment variable lies in the shapes and/or dimensions of the frame itself. The frame can in fact comprise geometries (rebounds or loops or edges or points of attachment or anchors or reliefs, for example in the region of the annulus) which in particular permit an additional adjustment of the interstitial space existing between the frame and the stent/bioprosthesis at the native annulus. Another adjustment variable is the diameter of the stent. Another adjustment variable is the diameter of the bioprosthesis itself.

Advantageously, the covering by the sealing skirt for filling the interstitial space can itself be optimized (e.g. tension, fold or return, skirt comprising various sub-sections, etc.). The sealing skirt between the stent/bioprosthesis and the frame can in particular retain a certain elasticity (or tolerance) in order to allow the frame to apply exactly to the morphology of the tricuspid annulus, without exerting stress.

BRIEF DESCRIPTION OF THE DRAWINGS

Other features and advantages of the invention will become clear from the following description and from the figures of the attached drawings, in which.

DETAILED DESCRIPTION OF THE INVENTION

Figure 1A:
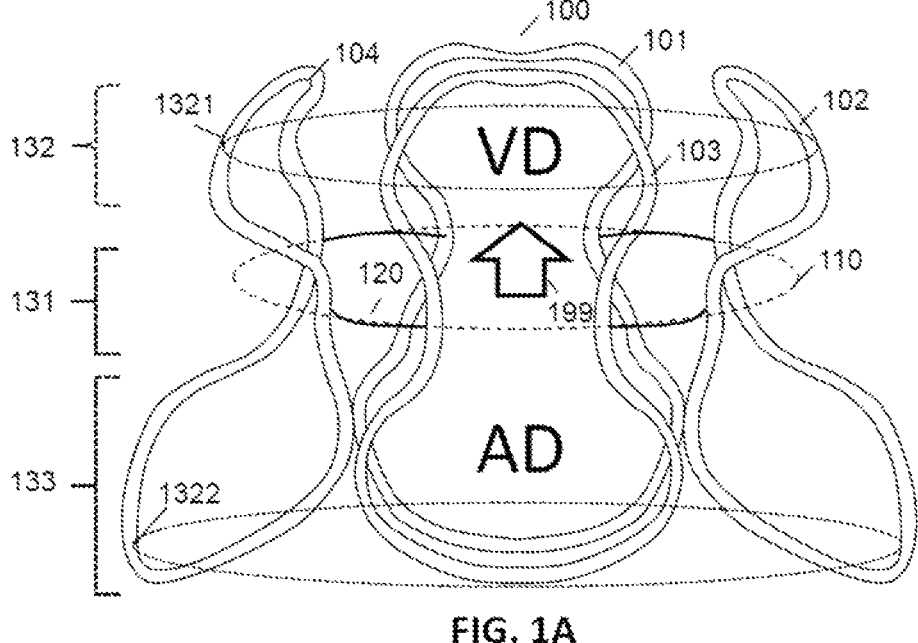
FIG. 1A shows an example of the frame according to the invention.

The tricuspid valve has specific features compared to the mitral valve, which features are set out in detail below, in particular in terms of the actual structure (e.g. geometry) and the environment in which it is put in place.

From the point of view of geometry, the mitral and tricuspid valves are in themselves very different. The tricuspid atrioventricular orifice provides a communication between the right ventricle and the associated right atrium. It is equipped with an atrioventricular valve, formed of three leaflets, namely the anterior, septal and posterior leaflets, which are of different dimensions. The mitral valve for its part is composed of two valves or leaflets (anterior and posterior). The tricuspid valve is the largest of the four heart valves, its surface area varying from 5 to 8 cm$^2$ (whereas the surface area of the mitral valve is of between 4 and 6 cm$^2$). The annulus of the tricuspid valve has a shape that is more elliptical or ovoid than circular. Its fibrous structure is incomplete, in the shape of a horseshoe situated in the septal region, which is more solid. In cases of tricuspid insufficiency, the less solid anterior (and in part posterior) region distends. Its diameter is variable, of the order of 30 to 32 mm. The tricuspid valve has a circumference of approximately 120 mm in men and of approximately 105 mm in women. It is formed of three elements: the valvular web (the 3 leaflets), the tricuspid annulus and the sub-valvular apparatus (papillary muscles and tendinous chords). By contrast, the mitral valve has a diameter of 28 mm/m$^2$ in diastole. It is of conical shape, of the order of 30 mm at the annulus and of 26 mm at the summit of the valves (leaflets). Its circumference is between 90 and 100 mm in women and between 100 and 110 mm in men.

Still from the point of view of geometry, the environments of the mitral and tricuspid valves are very different. In the right heart (composed of the right atrium and of the right ventricle), the right atrium is the confluence of the venous blood charged with $CO_2$ from the two venae cavae. The inferior vena cava has a diameter of approximately 30 millimeters (mm). The right atrium is more spacious than the left atrium, its capacity (or volume) being approximately 160 ml, whereas the left atrium has a volume of approximately 140 ml. The length of the right atrium is approximately 4.5 centimeters, the length of length of the left atrium is 3.5 centimeters. The structural aspects of the right and left ventricles are contrasted. The right ventricle has a thickness of 5 to 6 millimeters, while the left ventricle has a thickness of 12 to 14 millimeters. The mean pressure of the right ventricle is 15 mmHg, while it is 100 mmHg in the left ventricle. The blood pressure is about five times higher in the left ventricle than in the right ventricle.

The pressure gradient during diastole between the right atrium and the right ventricle is below 2 mmHg. The tricuspid valve corresponds to the atrioventricular orifice situated in the circulatory system functioning at low pressures.

The weight of the right ventricle is approximately 70 g, while the weight of the left ventricle is approximately 150 g. The wall of the right ventricle is thus substantially more fragile than that of the left ventricle. When a bioprosthesis valve system is implanted between the right atrium and the right ventricle, it is advantageous to provide relatively little anchoring means on the side toward the right ventricle (filling chamber of the right ventricle) and instead to focus the fixing on the atrial side toward the right atrium (in terms of the mitral valve, the anchors are generally placed under the mitral annulus on the side toward the left ventricle).

Consequently, these anatomical and physiological differences between the mitral valve and the tricuspid valve entail a significantly different mechanical or structural configuration (especially in terms of turbulence, regions of recirculation of the blood flow, mechanical stresses and forces, resistance of the materials and/or stability of the replacement assemblies, surgical replacement procedures, etc.). The embodiments take account and advantage of these anatomical differences of the valves and of their environment; they are advantageous especially in terms of blood flow, resistance, stability, access, placement, and holding in position.

The drawings provided are indicative. For example, the shapes of the frame and the size of the interstitial space have sometimes been exaggerated in order to make the invention easier to understand, for reasons of readability. In particular, the hook shape of the lower part of the frame has been exaggerated. The function of the shape alone is important in fine, and reference is made to the passages which detail the intended functions of the different parts of the frame.

FIG. 1A (with the right atrium labeled AD and the right ventricle labeled VD) shows an example of the frame according to the invention. In the example, the frame 100 comprises a plurality of parts formed from a metal alloy (for example a heat-sensitive or shape-memory alloy, such as a nickel-titanium alloy or nitinol).

Nitinol has the particular ability to change its physical state due to a variation in temperature, making it a material of choice in the clinical field (packaged in a frozen or cooled liquid, nitinol then retains its final shape after its release in the bloodstream at 37° C.).

The frame is of generally cylindrical shape with three parts of different diameters, allowing it to position itself and to maintain its position through the annulus of the tricuspid valve, without impeding the blood flow through the tricuspid valve. In one embodiment, the frame comprises at least four elements (101, 102, 103, 104). The frame has an overall height of between 32 mm and 45 mm (i.e. adapted to the dimensions of the bioprosthesis). A bioprosthesis 110 is placed inside the frame.

The four main parts of the frame 101, 102, 103 and 104 are interconnected in the region of the valve annulus, which is the narrowest, by a junction or a flexible and deformable hinge. In one embodiment, the main parts are made of a nickel-titanium shape-memory alloy. Each of the main parts is schematically in the form of a capital S. The flexible and deformable hinge measures between 5 and 7 mm in height, corresponding to the height of the valve annulus.

Figure 1B:
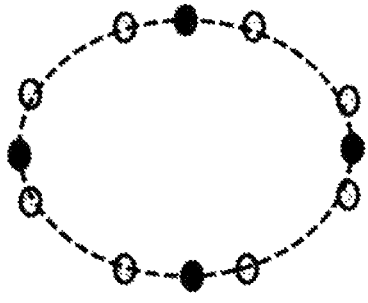
FIG. 1B illustrates an example of the interconnection of the sub-sections of the frame.

FIG. 1B illustrates an example of the interconnection of the sub-sections of the frame 100 according to one embodiment. In one embodiment, a (single) junction wire 110 connects the various main parts of the frame, for example by welds. In one embodiment, the main parts of the frame are connected by a plurality of junctions or hinges (this latter embodiment makes the structure according to the invention more flexible). The embodiments of these hinges advantageously permit an adaptation of the diameter of the frame considered as a whole, by making this diameter variable and/or configurable. In alternative embodiments, the number of direct contact points can in particular be adjusted (for example increased), so as to enlarge the surface area of contact with the native annulus and to improve the hold of the structure replacing the tricuspid valve. The example shown in FIG. 1B has twelve contact points. This type of configuration advantageously makes it possible to reduce the risk of peri-prosthetic leaks between the frame and the native tissue of the tricuspid annulus.

FIG. 1A shows that the frame according to one embodiment of the invention comprises three parts or regions. The direction of the blood flow is illustrated by the arrow 199.

In the region of the native cardiac annulus 131, the frame 100 is extensible and/or deformable. By virtue of its radial force (for example prestressed, or resulting from the mechanical play of the four interconnected parts), the frame 100 adapts to the morphology of the tricuspid annulus (which is not entirely circular and is often an ellipse). The native annulus, or the frame in its narrowest part, measures between 40 and 42 millimeters. This diameter can reach 45 mm, or even more that 50 mm in cases of significant dilation, corresponding to the anatomical region of the tricuspid annulus delimiting the passage or the orifice between the right atrium and the right ventricle. The annular region (of the native tricuspid annulus of the frame according to the invention) measures 5 to 7 mm in height.

In the region 132 within the right ventricle, the frame continues downstream in the right ventricle in the direction of the blood flow. In one embodiment, the frame extends in the right ventricle over a height of between 10 and 12 mm, flaring on the right ventricular side (i.e. has a convex shape). The maximum diameter 1321 in the portion within the right ventricle is slightly greater than the diameter in the region of the annulus. At its distal part in the right ventricle, the end of the frame terminates with a diameter having a value substantially equal to the diameter of the bioprosthesis (for example 35 mm or 40 mm). This mechanical configuration (i.e. convex shape and selection of diameters) advantageously allows the three leaflets forming the native tricuspid valve to be held in the open position without creating an obstacle, in the filling chamber of the right ventricle, to the flow of blood (no right ventricular outflow obstruction).

Located in the region 133 within the right atrium, situated upstream from the region of the annulus, is the proximal portion of the frame, positioned in the right atrium. In one embodiment, the frame has a convex flared shape. In one embodiment, the largest diameter 1332 is 6 to 8 mm greater than that of the region of the annulus. For example, the value of the diameter can be 50 mm if the annulus measures 42 mm. In this region 133 within the right atrium, the frame extends over a variable distance depending on the dimensions of the bioprosthesis. For example, this distance can be of the order of 15 mm. This region of the frame within the right atrium corresponds to the region of attachment to the stent containing the bioprosthesis.

Figure 2A:
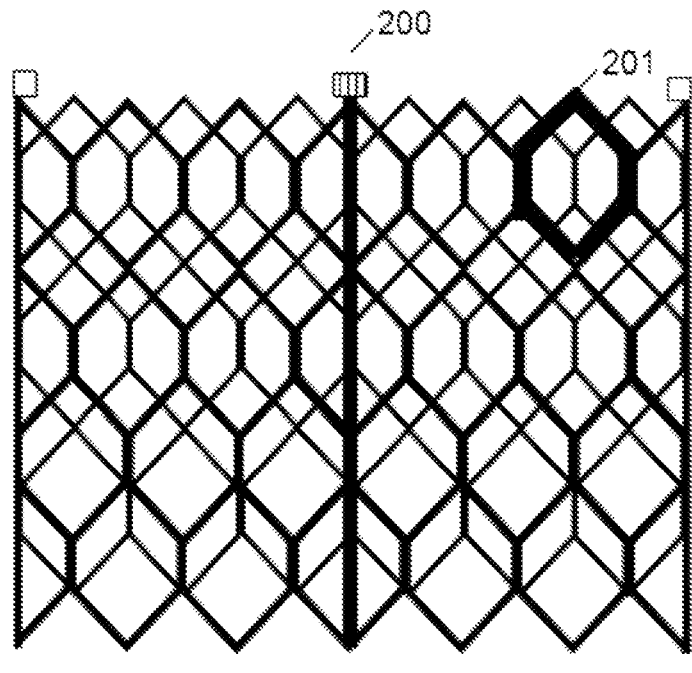
FIG. 2A shows a stent according to the prior art.

FIG. 2A shows a stent 200 according to the prior art. In one embodiment of the invention, the stent 200 used is a self-expanding stent. The stent 200 is cylindrical, formed of multiple cells 201 of metal alloy, for example an alloy identical to that of the frame 100 (titanium-nickel). The diameter of the stent 200 can be slightly smaller than that of the frame in the region of the annulus. The dimensions of the stent 200 are generally discrete: the standard dimensions are 30, 35 and 40 mm. The dimensions of the stent correspond to the dimensions of the bioprosthesis 210 (the stent 200 carries the bioprosthesis 210).

Figure 2B:
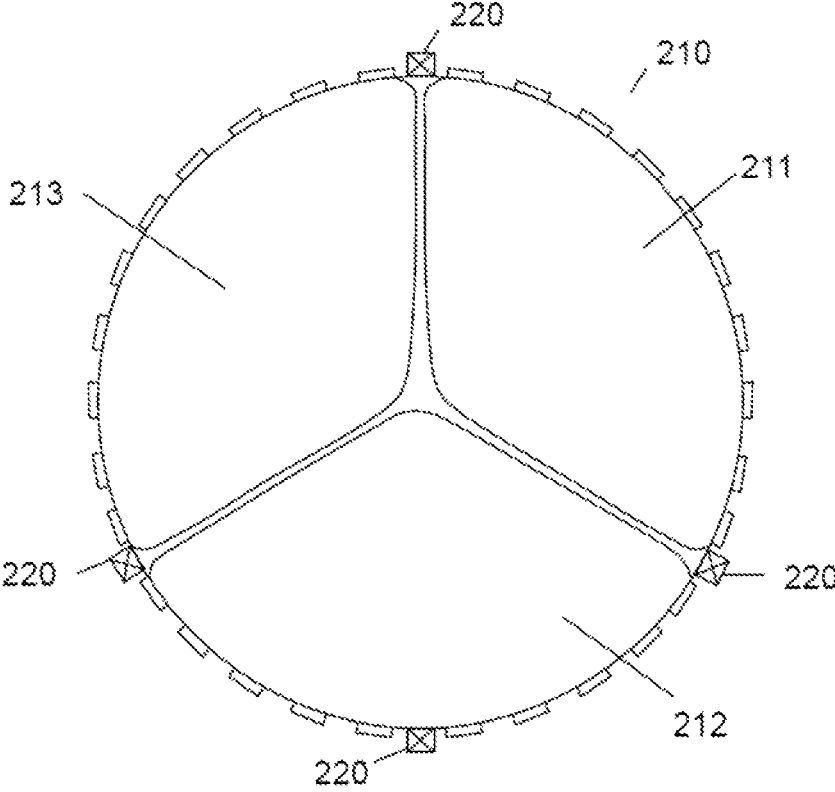
FIG. 2B shows a tricuspid valve bioprosthesis according to the prior art.

FIG. 2B shows a tricuspid valve bioprosthesis 210 according to the prior art. A tricuspid bioprosthesis is formed of three cusps (211, 212, 213) made from animal tissue (for example a bovine or porcine pericardium) and/or a synthetic fabric. The three cusps or "leaflets" forming the bioprosthesis are linked (e.g. associated or fixed or attached or welded or sewn) in or on or by or via the stent. The bioprosthesis functions in the physiological direction of the blood flow arriving in the right atrium and injected in systole into the filling chamber of the right ventricle.

Various techniques can be employed to link the stent and the bioprosthesis to the different contact points 220 (e.g. welding, gluing, fixed link or spring, flexible or partially rotary contact points, etc.). In one embodiment, three contact points 220 are used, permitting more secure fixing of the tricuspid valve. In one embodiment, a plurality of contact points (greater than or equal to four) retain the bioprosthesis in the stent. The probability of failure generally decreases as the number of contact points increases.

Figure 3A:
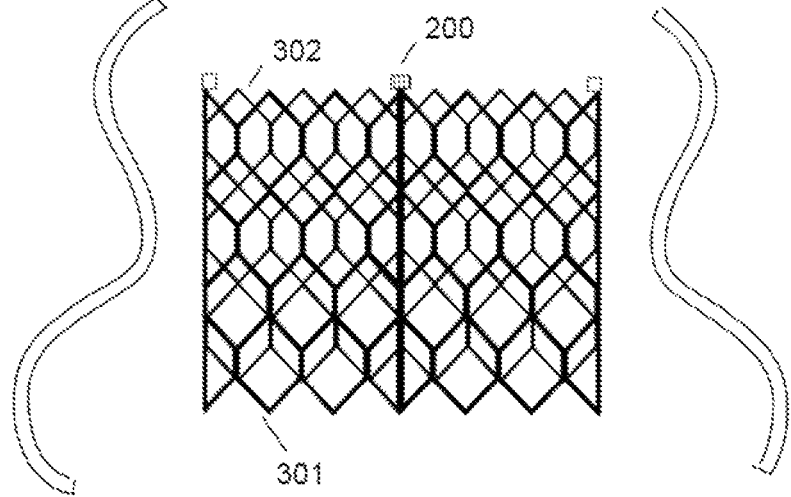
FIG. 3A is an illustration of the relative positioning of the frame with respect to the stent carrying the bioprosthesis.

FIG. 3A is an illustration of the relative positioning of the frame 100 with respect to the stent 200 carrying the bioprosthesis 210. In one embodiment, the stent containing the bioprosthesis is positioned inside the frame. The proximal end 301 (i.e. the base) of the stent is situated in the right atrial region 133 of the frame. The bioprosthesis 210 is therefore predominantly in an infra-annular position. The distal end of the stent 302 containing the bioprosthesis 210 is situated in the region 132 within the right ventricle, but only by a few millimeters. The stent is thus positioned in an asymmetrical position with respect to the region of the annulus, which is the narrowest part of the frame.

Figure 3B:
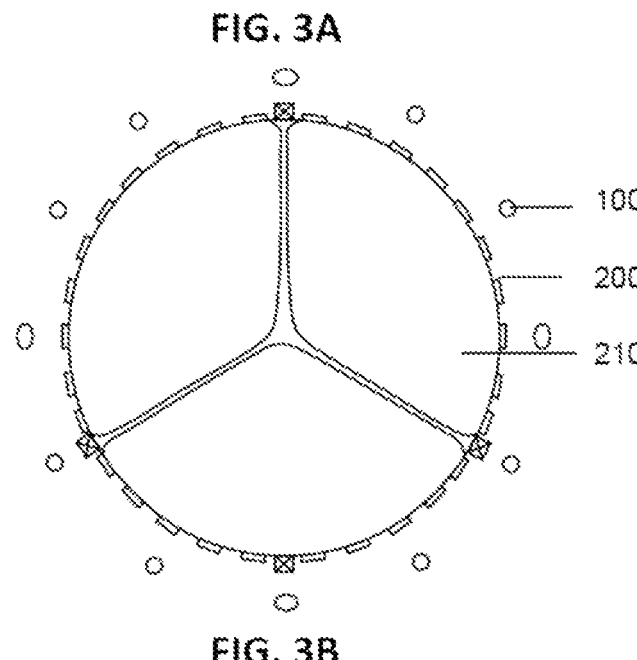
FIG. 3B shows a horizontal sectional view at the height of the region of the annulus.

FIG. 3B shows a horizontal sectional view at the height of the region of the annulus. The figure shows the presence of the frame 100, the stent 200 and the bioprosthesis 210.

Figure 4A:
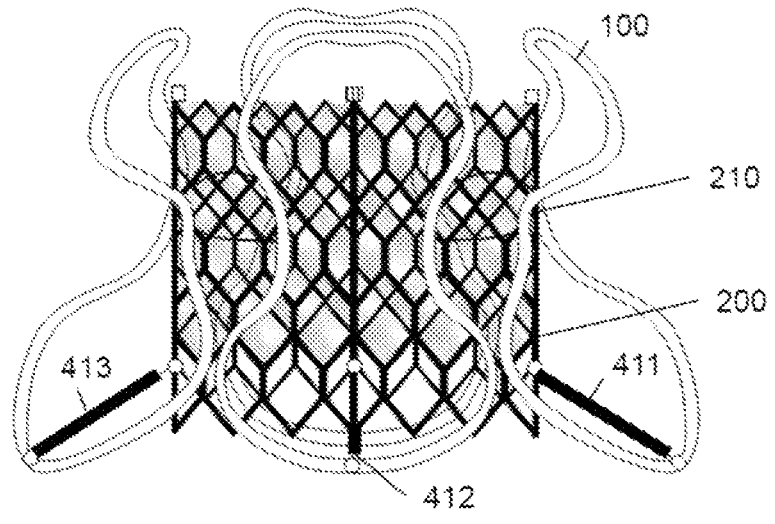
FIG. 4A shows an example of the assembly according to the invention.

FIG. 4A shows an example of the assembly according to the invention.

The frame 100 is connected by one or more strands to the stent 200 comprising the prosthesis 210.

The number, location and nature (e.g. materials) of the strands are variable according to the embodiments (assembly more or less flexible, more or less stable or maintained, more or less disruptive to the circulation, etc.).

In a particular embodiment, a single fixing strand can suffice (the transmission of the mechanical forces via this single strand, optionally reinforced, can be modeled and optimized). Advantageously, the blood flow is disturbed a minima.

Configurations with two or three strands are possible.

In the example illustrated in the figure, four strands 411, 412, 413, 414 hold the stent to the frame.

In one embodiment, the four strands of the example shown in the figure join the stent 200 (in its region 132 within the right atrium) to the base of the frame 100 (in its widest region, i.e. in the region 132 within the right atrium). This configuration, in which the attachment is made upstream of the circulation of the blood flow, has the advantage of providing torsional stability of the stent downstream. According to one embodiment (not shown), in addition to or instead of the attachment upstream of the valve and via the base of the stent, one or more additional and optional attachments of the stent to the frame can be made in the region of the annulus, or via the distal part of the stent (even if the latter penetrates little into the right ventricular region).

In one embodiment, one or more strands (or "tabs") are made of nitinol. Generally, heat-sensitive and/or shape-memory materials can be used.

In one embodiment, one or more strands are rigid. In some embodiments, one or more strands are elastic or flexible or deformable. Other embodiments combine elastic strands and rigid strands (e.g. depending on the dynamic behavior of the structure of the assembly). Other advanced embodiments involve the use of actuatable or configurable strands.

Figure 4B:
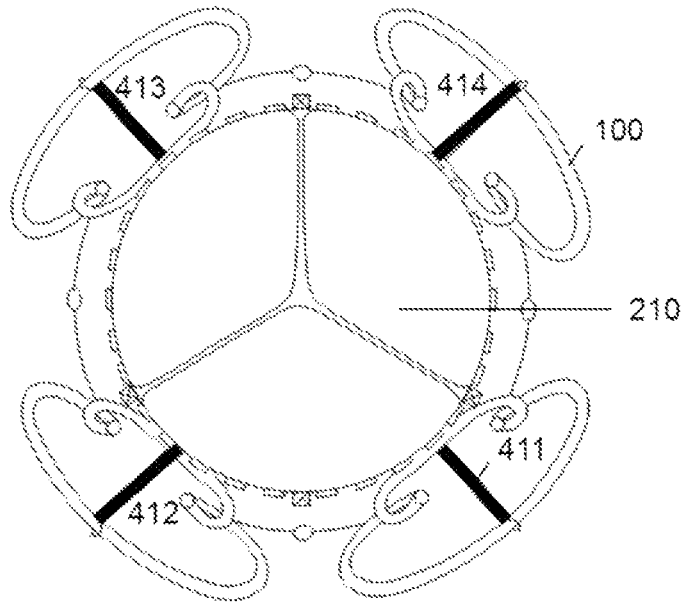
FIG. 4B shows a plan view of an example of the assembly according to the invention.

FIG. 4B shows a plan view of an example of the assembly according to the invention. The figure shows in particular the placement of the bioprosthesis 210 within the frame 100.

Figure 5A:
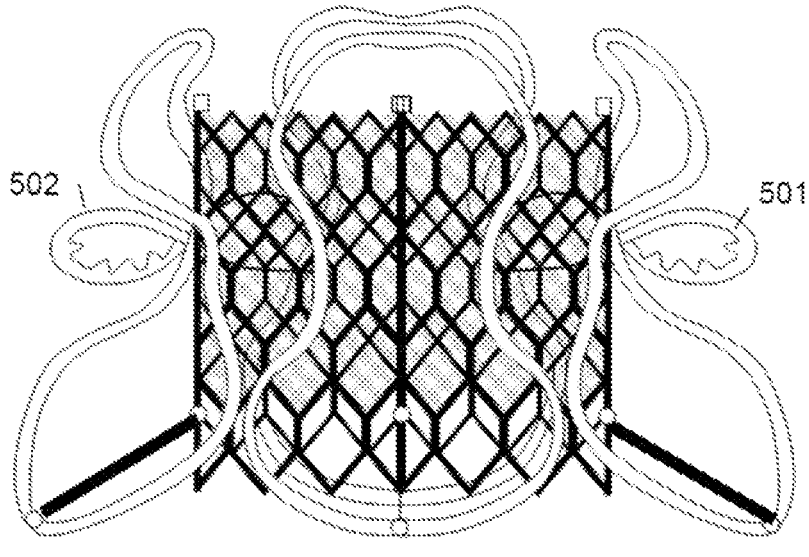
FIG. 5A illustrates an alternative embodiment of the invention.

FIG. 5A illustrates an alternative embodiment of the invention. The assembly has one or more optional fixing elements (i.e. for retention in the heart). In one embodiment, a fixing element has the form of a "racket" or a "loop" or a "tab" (for example 501). In one embodiment, a fixing element is made of an alloy of nitinol. A fixing element has a height of the order of 8 to 10 mm and a length of between 10 and 12 mm. In one embodiment, one or more of these optional fixing elements are joined to the frame 100 in the annulus region 131 and open only on the atrial side. In some embodiments of the invention, no fixing element is used. In one embodiment of the invention, a single fixing element is used. In one embodiment of the invention, two fixing elements are positioned symmetrically. For improved stability, a second fixing element can in fact be positioned (for example symmetrically, e.g. toward the inter-atrial septal wall). However, this configuration may in some cases increase the risk of impaired electrical conduction (including atrioventricular block). In one embodiment, a plurality of fixing elements are used, decreasing the risk of impaired conduction.

The technical effect (the function) of such fastening elements is in particular that of stabilizing and fixing the frame 100 in the heart. In particular, these fixing elements improve the stability of the assembly according to the invention in rotation and/or torsion and/or translation.

Figure 5B:
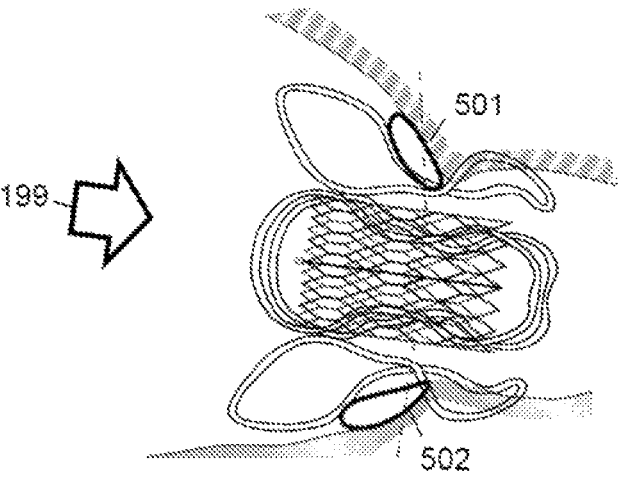
FIG. 5B specifies the anatomical positioning of the optional fixing elements.

FIG. 5B shows the anatomical positioning of the optional fixing element. The retaining loops are placed upstream of the blood flow 199. In the embodiment shown in FIG. 5B, the assembly comprises two fixing elements 501 and 502. These elements are arranged diametrically opposite with respect to the frame. Each element is disposed substantially perpendicular to the frame and bears on the wall of the native tissue. One of the fixing elements 501 is positioned on the side of the interatrial septum, while the other fixing element 502 is positioned toward the outer wall of the right atrium (called the pectinate muscle). According to the embodiments, the technologies used to attach the fixing elements to the frame are variable. For example, the attachment points can be welded. From a dynamic perspective, the plurality of fixing elements deploy spontaneously or automatically outward during the release of the frame upon removal of the catheter in which the whole system is delivered.

Figures 6A, 6B:
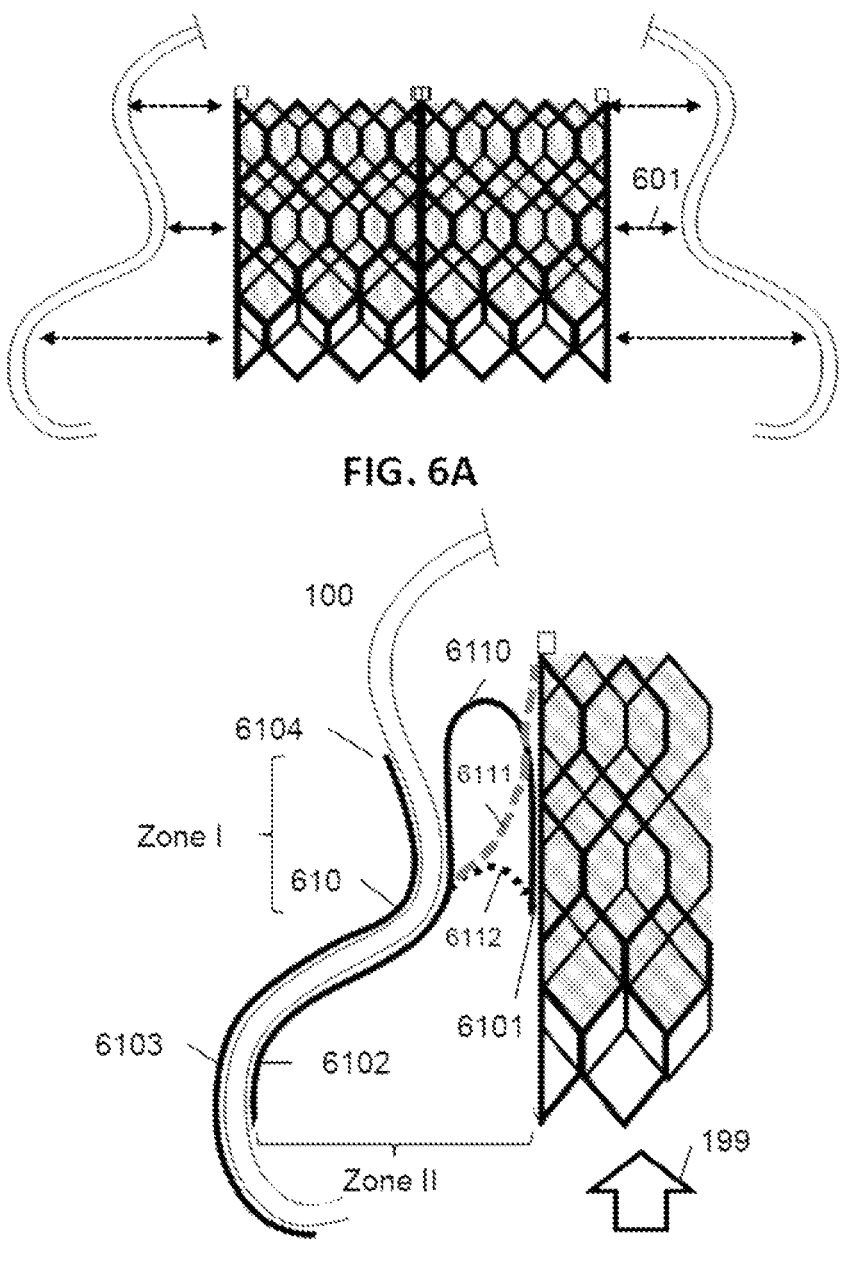
FIG. 6A illustrates the circumferential spacing or interstitial space between the stent and the frame.
FIG. 6B illustrates an alternative embodiment of the invention comprising a sealing skirt.
Figures 6C, 7B:
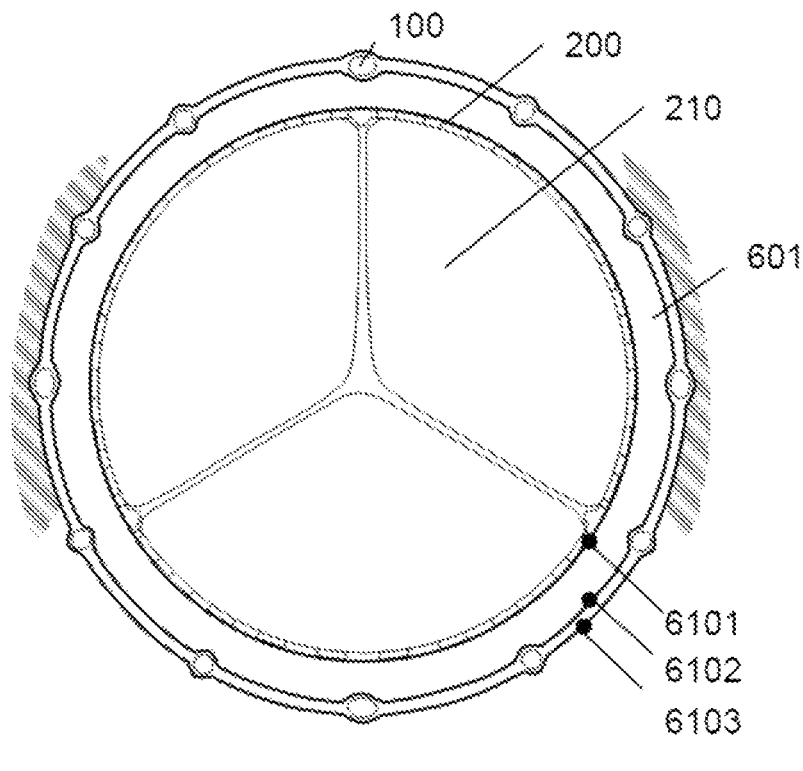
FIG. 6C shows a horizontal sectional view of an embodiment of the assembly comprising the frame, the stent carrying the bioprosthesis, and the sealing skirt.
FIG. 7B illustrates an optional embodiment comprising a stent disposed in the inferior vena cava and connected to the assembly by a flexible link made of nitinol, with a radiopaque marker fixed to the frame in the right atrium.

FIG. 6A illustrates the circumferential spacing or interstitial space between the stent and the frame. In the region of the native annulus, there is in fact a free circumferential space 601 of variable amplitude between the stent 200 and the frame 100. The function of the frame 100 is in particular to maintain and rigidify the whole system while applying a radial force against the native annulus to ensure a steady placement in the heart. The stent and the bioprosthesis are of cylindrical shape (of discrete and standardized sizes). The diameter of the stent and the diameter of the bioprosthesis are substantially equal and are less than the diameter of the frame, and there is therefore an interstitial space (a gap) between the frame 100 and stent 200.

FIG. 6B illustrates an alternative embodiment of the invention comprising a sealing skirt (sectional view).

Many alternative embodiments are possible for the positioning and the nature of this sealing skirt.

The function of the sealing skirt is to seal (in particular in the region of the atrioventricular annulus) the assembly according to the invention (i.e. the system formed of the frame and of the stent carrying the bioprosthesis); in particular, the sealing skirt minimizes the risk of peri-prosthetic leaks (item 6104 below).

The sealing skirt 610 generally bears on the frame and at least partially covers the stent 200.

In one embodiment, the starting point 6101 for fixing the sealing skirt 610 is sewn (or bonded) on the outer wall of the stent over a height that broadly covers the region of the annulus. The fabric of the sealing skirt is then folded (for example turned back 180° to the outside) in order to descend along the inner wall of the frame 6102. Finally, by way of its intra-atrial base, the fabric of the sealing skirt envelops the frame 100 by ascending the outer wall of the frame 6103, in order to terminate above the region of the annulus which is sewn or glued to the capital S-shaped articulations and/or the elements of the frame 100, thereby reinforcing this frame in the narrowest region pressed against the native tissue 6104. This point 6104 in particular plays a decisive role in preventing peri-prosthetic leaks. Regarding the alternative embodiments, it is not necessary for the sealing skirt to envelop the frame completely.

In one embodiment, the sealing skirt is formed of a synthetic material (for example polyethylene terephthalate or PET, which is a flexible material that is impervious to water or to blood). In one embodiment, a leaktight material such as Dacron may advantageously be used. The skirt can be composed of a plurality of materials, for example arranged in layers and/or strips (i.e. with reinforced regions for example and/or with regions composed of a single layer and/or openworked spaces ("openings", "holes", porous or pervious sub-sections, etc.) upstream from the region of the annulus, on the atrial side, in order to minimize the thickness of the assembly during packaging.

The structure of the skirt (e.g. materials, arrangement of the sub-sections, layers, distribution of the openworked spaces, etc.) can in particular be effected so as to optimize (i.e. to minimize the thickness of the assembly during packaging and/or to ensure the resistance to blood flow of the skirt thus structured and/or to contribute to reinforcing the hold of the assembly put in place, e.g. stability in rotation and/or translation).

From upstream to downstream, from the right atrium to the right ventricle, the blood flow is slightly modified by the assembly according to the invention. Upstream, on the atrial side, the convex structure of the frame entails some turbulence of the blood flow, but this change is acceptable or of no medical or mechanical significance. The patient is under treatment with anticoagulants in order to prevent clot formation caused by the presence of the bioprosthesis and of its frame. As a result, the blood rheology is modified.

In zone I in FIG. 6B ("contact" region or space), blood flow is "blocked" (or stopped or blocked or obstructed or prevented) or at least substantially minimized in the region of the native annulus (i.e. over the entire circumference and at least partially over the height of the corresponding cylinder of the heart valve annulus.

In zone II in FIG. 6B ("interstitial" region or space), the skirt captures the blood flow and channels it through the bioprosthesis, on account of its leaktightness. The shape of the fold 6110 (FIG. 6B) may incidentally influence the recirculation in the direction of the bioprosthesis. Some advantageous embodiments involve "tightening" or "slackening" this fold of the skirt to a greater or lesser extent in such a way as to optimize the dynamic flow of the blood flow. There is a slight obstruction to the blood flow around the perimeter of the valve itself, because the diameter of the bioprosthesis is in reality very slightly smaller than the diameter of the native annulus. The latter, however, is dilated by the pathology justifying the replacement of the tricuspid valve, which makes this particular obstruction negligible in proportion. In the region of the annulus, the frame is applied (with contact) to the native tissue. Leaks between the frame and the native tissue are in practice non-existent or insignificant (i.e. due to the absence of calcification of the tricuspid annulus, which does not permit the formation of interstitial spaces between the frame and the native tissue, and also because the fabric of the skirt forms a fold in the region of the annulus, which improves the leaktightness in this region). A triple thickness (of material (e.g. of PET)) seals the prosthetic system, advantageously eliminates para-prosthetic leaks between the prosthesis and the native tissue, but may increase the thickness of the assembly in its folded configuration. Alternative embodiments allow these requirements to be reconciled by moving the folding regions or by arranging the various components of the assembly in such a way as to optimize its geometric folding.

Some embodiments of the invention provide the use of strands and/or stent meshes having a tubular or cylindrical or elliptical shape, so as to minimize the impacts caused to the red blood cells. In one embodiment, the sections of the strands and/or of the stent meshes are elliptical and are oriented (like "aeronautical flaps") in such a way as to improve the rheology and/or to optimize the local and/or global blood flow. Finally, downstream from the ventricular side, the flow is partially channeled by the stent without causing any medically adverse effect (in particular this does not create any obstruction to the blood flow entering the right ventricle. Downstream of the annulus, the frame is wider (outwardly oriented convex shape) but of smaller diameter than the upstream region, so as not to impede the ejection path to the pulmonary valve situated in the right ventricle at approximately 10 mm.

Figure 7A:
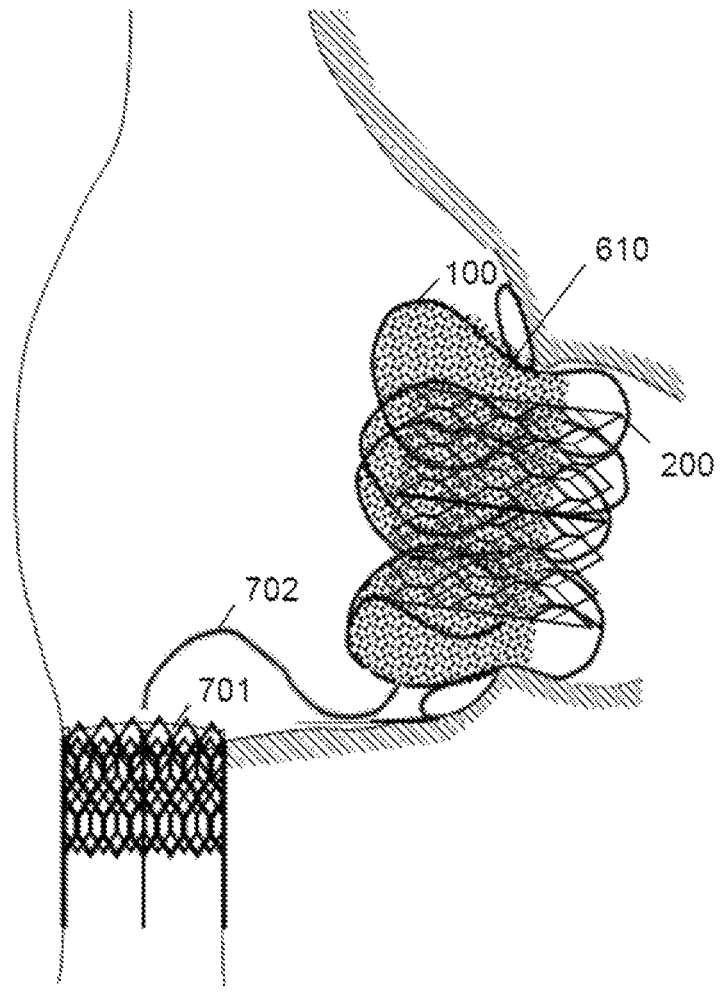
FIG. 7A illustrates an alternative embodiment of the invention.

FIG. 7A illustrates an entirely optional alternative embodiment of the invention comprising additional fixing to a stent positioned in the inferior vena cava.

In some infrequent anatomical situations, it may happen that the tricuspid annulus—most often dilated—has no stable attachment region or calcification region. In these precise cases, it is advantageous to put specific, additional and optional fixing devices in place, and the combination of these with the assembly according to the invention improves the retention and hold (e.g. in translation) of the assembly according to invention.

According to this alternative embodiment, a self-expanding stent 701 (for example made of nitinol) is placed in the inferior vena cava, at a distance from the frame. The stent 701 is of variable diameter, generally of the order of 30 mm, adapted to the size of the inferior vena cava at its anastomosis into the right atrium. Compared with the additional fixing means provided for the mitral valve, the stent placed in the inferior vena cava must be shorter, so as not to interfere with the circulation in the suprahepatic veins. In other words, the arrangement of the securing means in the case of the tricuspid valve is also specific when compared to the arrangement for the mitral valve. The stent 701 is connected to the frame 100 in various ways (for example by a wire link 702). The wire link 702 is connected to the stent 701 in the upper part thereof, flush with the anastomosis of the inferior vena cava. The wire link 702 is connected to the main frame at the intra-right-atrial base in the lower part thereof. This wire link 702 can be made visible in fluoroscopy by a radiopaque marker. This flexible and deformable wire link can be rectilinear or undulating. It can be adapted in its length (plus or minus 30 mm, depending on the anatomical distance between the tricuspid annulus and the inferior vena cava).

Figure 8:
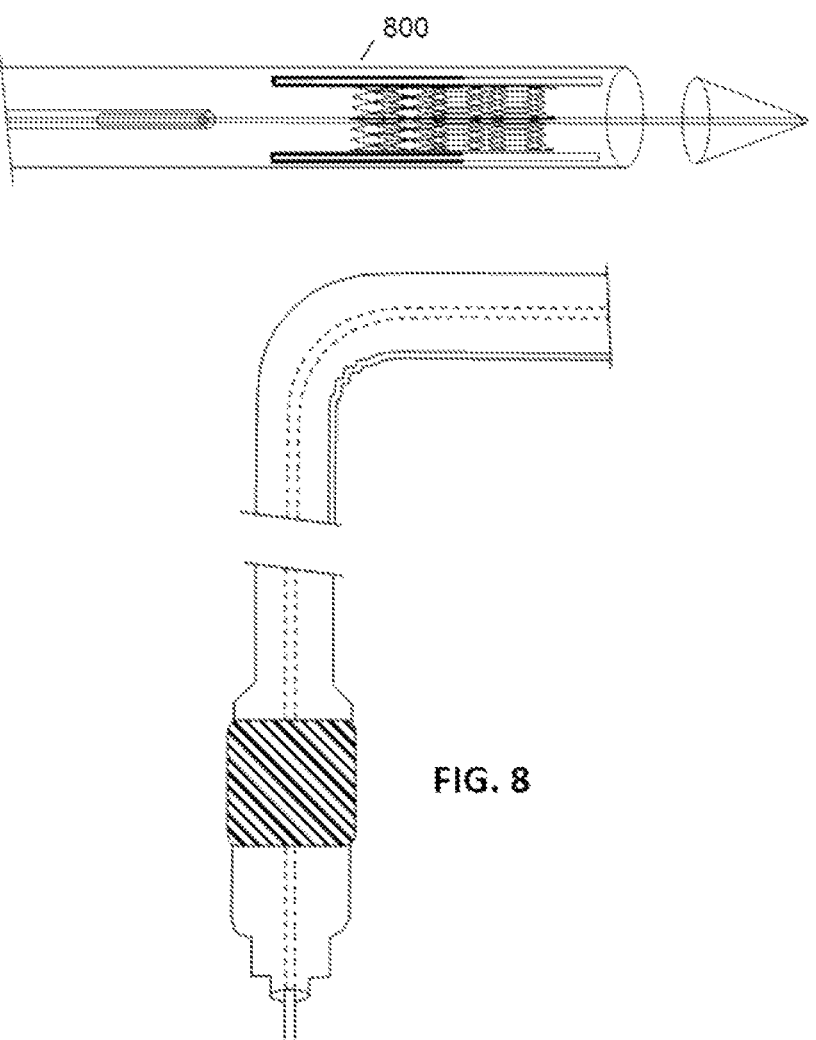
FIG. 8 illustrates the method by which the assembly according to the invention is put in place.

FIG. 8 illustrates the method of placement of the system or assembly according to the invention. In a first state called "folded" or "compressed" or "packaged", the delivery catheter 800 (or "delivery system") contains the frame, the stent and the bioprosthesis (and also, where appropriate, the fixing elements and sealing skirt according to the alternative embodiments). In a second state called "relaxed" or "released" or "uncompressed", the assembly according to the invention deploys in the patient's heart (by manipulation on the part of the operator).

In one embodiment of the invention, the bioprosthesis is "folded" in the stent, which is itself "folded" (with the sealing skirt) in the frame in a packaging state.

Different embodiments of the "release" of the assembly according to the invention are described below. The instrument and the release device or "delivery system" comprises: a) a 0.35 inch guide of suitable length (length close to 280 mm) curved in a "snail shape" at its non-traumatic distal end, adapted to be placed in the cavity of the right ventricle; b) a catheter with a length adapted to the distance of the common femoral vein (at the inguinal hollow) to the right atrium and the right ventricle. This catheter or sheath formed of a coaxial tube and referred to as an over-the-wire catheter is centered on the 0.35 inch guide. At its distal part, this catheter has a retractable sheath. Its diameter of 18 to 24 French is suitable for the assembly according to the invention. The sheath is preceded at its distal end by an atraumatic conical tip adapted to receive the 0.35 coaxial guide provided to cross the tricuspid valve and be placed in the tip of the right ventricle; c) a handle which contains the mechanism for releasing the bioprosthesis. This handle is welded to the coaxial tube. It controls the deployment of the assembly. The handle has a knurled screw controlling the deployment and release of the assembly. The device is also provided with a system for bending and guiding the tube at its distal end, ahead of the sheath that contains the assembly according to the invention.

The method for deploying and releasing the assembly according to the invention is described below. The sheath (18 to 24 Fr) is retractable and contains the assembly according to the invention (according to its possible variants). In a first step, a 24 Fr desilet adapted to receive the introducer system is put in place percutaneously in the common femoral vein. In a second step, the 0.35 guide is placed in the tip of the right ventricle. In a third step, the introducer system containing the frame and the bioprosthesis is passed through the desilet, then pushed through the inferior vena cava to the right atrium, on the 0.35 guide. In a fourth step, on arrival in the right atrium, the sheath is bent at its end toward the tricuspid orifice, by way of the mechanical handle. In a fifth step, the assembly is then pushed across the tricuspid valve. In a sixth step, the frame is gradually deployed under fluoroscopy (radiopaque markers are located on the frame at the height of the region of the annulus) and transesophageal echocardiography and/or 3D control. The knurled screw of the handle rotating in the clockwise direction gradually releases the bioprosthesis-containing frame under transesophageal echocardiography and fluoroscopy. In a seventh step, after the region of the annulus, in the part within the right atrium, the deployment continues, releasing one or more fixing elements ("hooks", "rackets", "loops") which press against the outer wall of the atrium and the inter-atrial septum. At the same time, the bioprosthesis is released and begins to function as soon as the part of the frame within the right atrium is fully released. In an optional step corresponding to an embodiment comprising the placement of a fixing stent in the inferior vena cava, the sheath is progressively withdrawn in the anastomosis orifice of the inferior vena cava, releasing the stent fixed to the frame by a strand made of nitinol. This is done under transesophageal echocardiography and fluoroscopy and with radiopaque contrast medium. Finally, a step of angiography and transesophageal echocardiography verifies the leaktightness, that is to say the absence of leakage of the bioprosthesis in place in the native tricuspid valve.

In some embodiments of the invention, the assembly can be instrumented by comprising sensors (for example active sensors of one or more passive markers) and/or actuators.

The assembly according to the invention can in particular comprise radiopaque markers for quantifying, measuring and verifying the correct positioning of the assembly in the patient's heart.

Additionally or alternatively, the assembly according to the invention can also comprise devices which permit movement or spatial readjustment of the assembly, the position of which may change or even drift over time.

In other words, the assembly according to the invention may be static in some embodiments and/or dynamic or adaptive in other embodiments. The assembly according to the invention can in particular comprise one or more microelectromechanical systems. A microelectro-mechanical system is a microsystem of generally micrometric dimensions comprising one or more mechanical elements using electricity as an energy source in order to realize a sensor and/or actuator function. In alternative embodiments, biomedical microelectromechanical systems are used. The actuators can be placed in or on different parts of the frame and/or at the attachment regions of the different sub-sections of the frame and/or in or on the strands attaching the frame to the stent.

The actuators can in particular be used, for example, to reconfigure the shape of the frame (for example its convexity) and/or to adjust the covering provided by the sealing skirt (e.g. curvature, return, tension of the skirt surface at certain places, etc.) and/or to adjust the fixation of the stent to the frame. The movements or spatial readjustments are generally effected over short distances. They can be reversible or irreversible (e.g. mechanical detents). They can be configured and/or configurable. They can be at least partially determined by an external device (controlled by the operating physician), i.e. in open loop. Logic devices and/or physical devices can secure the spatial modifications, if appropriate. The structural modifications made to the structure can also be controlled in a closed loop, for example according to the static position and dynamic behavior measurements of the inserted assembly in the blood flow.

In one embodiment, the assembly of the invention is modified so as to permit replacement of the mitral valve. The terms "tricuspid" and "mitral" are not generally interchangeable. In one particular embodiment of the invention, the assembly is modified to permit replacement of the mitral valve, taking into account the fact that the diameter of the pathological mitral valve is significantly less than the diameter of the pathological tricuspid valve. Among other static modifications, compared to the assembly for the tricuspid valve, preference will be given to the use, in addition to a mitral bioprosthesis, of a smaller number of sub-sections constituting the frame (e.g. a more easily obtainable mechanical stability) and, if possible, a smaller number of sealing skirt thicknesses in the packaged state.

The invention claimed is:

1. An assembly for a tricuspid orifice of a right side of a human heart, comprising
an external frame connected to
an internal stent carrying
a tricuspid valve bioprosthesis and
a sealing skirt,
wherein:
the external frame is configured to hold its position in a native tricuspid annulus between a ventricle and an atrium, the external frame having a ventricular end, an opposing atrial end and a middle portion, the external frame defining circumferential interstitial space between the external frame and the internal stent, the interstitial space between the internal stent and the external frame extending over an entire height of the internal stent;
the external frame having three zones of different diameters, the three zones comprising:
a first outward convex zone configured for arrangement in the ventricle;
a second outward convex zone configured for arrangement in the atrium, the second outward convex zone having a diameter greater than a diameter of the first outward convex zone;
a third zone separating the first and second outward convex zones and having a diameter smaller than the diameter of the first and second outward zones, the third zone being configured for arrangement at the annulus;
the internal stent has an atrial end, a ventricular end and a midportion therebetween, the internal stent is connected to the external frame by one or more fixing strands, the external frame and the internal stent being connected only by the one or more fixing strands;
the internal stent includes a plurality of rows of cells, a first row of cells of the plurality of rows of cells are formed having an elongated hexagonal shape, at least one row of cells of the plurality of rows of cells adjacent the first row of cells are formed having a generally rhombus shape;
each of the one or more fixing strands includes a first end and an opposite second end, the first end of each of the one or more fixing strands being coupled to the external frame, and the second end of each of the one or more fixing strands being coupled to the internal stent at the atrial end of the internal stent, at a position adjacent to the atrial end of the internal stent, or at the midportion;
the one or more fixing strands being flexible and ensuring the interstitial space between the internal stent and the external frame is maintained over the entire height of the internal stent; and
the sealing skirt comprises a fold extending from an interior surface of the third zone configured for arrangement in the annulus to the internal stent to cover the interstitial space existing between the external frame and the internal stent;
the sealing skirt is configured to obstruct a contact space between the external frame and a site of native tissue in a region of the native tricuspid annulus upstream of the annulus; and
the tricuspid valve bioprosthesis is operable to block flow in a direction from the ventricular end of the external frame to the atrial end of the external frame.

2. The assembly according to claim 1, wherein the external frame has a deformable region configured to hold the assembly in position inside the native tricuspid annulus.

3. The assembly according to claim 1, wherein the external frame has, upstream from the region of a native annulus, a shape configured to reinforce the hold of the assembly in the native tricuspid annulus.

4. The assembly according to claim 1, wherein the external frame has, downstream from a region of the native annulus, a shape configured to reinforce the hold of the assembly in the native tricuspid annulus.

5. The assembly as claimed in claim 1, wherein each of the one or more fixing strands is made of nitinol.

6. The assembly according to claim 1, further comprising at least one fixing element for fixing to the native tissue.

7. The assembly according to claim 6, wherein at least one of the frame, the internal stent, the one or more fixing strands, or the fixing element is composed of a heat-sensitive material, a shape-memory material, or a shape-memory material that is heat-sensitive.

8. The assembly according to claim 1, the sealing skirt being composed of several sub-sections, of several layers of materials, or of several sub-sections and several layers of material.

9. The assembly according to claim 1, further comprising at least one sensor, a radiopaque marker, or both the at least one sensor and the radiopaque marker.

10. The assembly according to claim 1, further comprising an actuator suitable for modifying a structure of the assembly, for adjusting a positioning of a part of the assembly with respect to the native annulus, or both for modifying the structure of the assembly and adjusting the positioning of the part of the assembly with respect to the native annulus.

11. The assembly according to claim 1, said assembly being connected to a further stent suitable for positioning in an inferior vena cava, said further stent being connected to the external frame of the assembly by a strand made of nitinol.

12. The assembly according to claim 1, said assembly being folded up in a packaged state in a catheter for introduction by a percutaneous route.

13. The assembly according to claim 1, wherein the first end of each of the one or more fixing strands are connected closer to the atrial end than to the ventricular end of the external frame.

14. The assembly according to claim 1, wherein the external frame extends outwardly with respect to the tricuspid valve bioprosthesis from the middle portion to the atrial end.

15. The assembly according to claim 1, wherein the external frame comprises a plurality of sub-sections that are independent of one another.

16. The assembly according to claim 15, wherein each of the plurality of sub-subsections comprises a loop, the loops not being interconnected with each other.

17. The assembly according to claim 1, wherein a diameter of the internal stent is on the order of 20% less than the diameter of the external frame in the region of the native tricuspid annulus.

18. The assembly according to claim 1, wherein the circumferential interstitial space between the external frame and the internal stent is a plurality of millimeters.

19. The assembly according to claim 1, wherein the external frame has a height greater than the height of the internal stent.

20. The assembly according to claim 19, wherein the atrial end of the external frame extends beyond the atrial end of the internal stent and the ventricular end of the external frame extends beyond the ventricular end of the internal stent.

21. The assembly according to claim 19, wherein the height of the external frame is between 32 and 45 mm.

22. The assembly according to claim 1, wherein the plurality of rows of cells includes a second row of cells adjacent the at least one row of cells on a side opposite the first row of cells.

23. The assembly according to claim 1, wherein the external frame includes an outer wall and an opposite inner wall facing the internal stent, and wherein the sealing skirt includes an inner portion, an outer portion, and an intra-atrial base portion connecting the inner portion and the outer portion, the inner portion covering a portion of the inner wall, the outer portion covering a portion of the outer wall, and the intra-atrial base portion covering the atrial end of the external frame so as to envelope a portion of the external frame.

24. A method for replacing the tricuspid valve, comprising steps of positioning the assembly as claimed in claim 1 in a folded state in a catheter, and introducing and deploying said assembly by a percutaneous route.

\* \* \* \* \*